United States Patent
Park et al.

(10) Patent No.: US 9,274,658 B2
(45) Date of Patent: Mar. 1, 2016

(54) METHOD FOR DETECTING BIOMOLECULES USING A CAPACITIVE TOUCH SCREEN

(75) Inventors: Hyun Gyu Park, Daejeon (KR);
Byoung Yeon Won, Daejeon (KR)

(73) Assignee: KOREA ADVANCED INSTITUTE OF SCIENCE AND TECHNOLOGY, Daejeon (KR)

( * ) Notice: Subject to any disclaimer, the term of this patent is extended or adjusted under 35 U.S.C. 154(b) by 130 days.

(21) Appl. No.: 14/000,403

(22) PCT Filed: Jan. 10, 2012

(86) PCT No.: PCT/KR2012/000220
§ 371 (c)(1),
(2), (4) Date: Sep. 13, 2013

(87) PCT Pub. No.: WO2012/115349
PCT Pub. Date: Aug. 30, 2012

(65) Prior Publication Data
US 2014/0022209 A1  Jan. 23, 2014

(30) Foreign Application Priority Data

Feb. 21, 2011 (KR) ........................ 10-2011-0015268

(51) Int. Cl.
*G06F 19/00* (2011.01)
*G06F 3/044* (2006.01)
*G01N 27/327* (2006.01)

(52) U.S. Cl.
CPC ............ *G06F 3/044* (2013.01); *G01N 27/3276* (2013.01)

(58) Field of Classification Search
CPC .................................................. G06F 19/3412
See application file for complete search history.

(56) References Cited

U.S. PATENT DOCUMENTS

| 2007/0149868 A1* | 6/2007 | Blank et al. .................... 600/316 |
| 2011/0027128 A1* | 2/2011 | Gridelet et al. ............ 422/82.01 |
| 2011/0050618 A1* | 3/2011 | Murphy et al. ................ 345/174 |

FOREIGN PATENT DOCUMENTS

| JP | 10-33512 A | 2/1998 |
| JP | 11-183377 A | 7/1999 |

(Continued)

OTHER PUBLICATIONS

Kwon, J., et al., "11.2. The touch screen panel types and feature", "Information and Communications Policy", Jul. 16, 2008, pp. 3-4, vol. 20.

(Continued)

*Primary Examiner* — Kent Chang
*Assistant Examiner* — Scott Au
(74) *Attorney, Agent, or Firm* — Hultquist, PLLC; Steven J. Hultquist

(57) ABSTRACT

There is provided a method of detecting biomolecules using a capacitive touch screen receiving a touch with a conductor as an input signal to perform an output on a display screen, and more particularly to a method of detecting target biomolecules by applying biomolecules having electrical conductivity to a touch panel and detecting a change in capacitance of a surface of a touch panel generated according to the concentration of the biomolecules.
A method of detecting biomolecule according to the present invention uses a capacitive touch screen capable of being cheaply manufactured on a large scale, such that the method may have advantages such as cheap cost and a short analysis time and simply detect biomolecules in a personal terminal such as a smart phone, a tablet PC, and the like, on which a capacitive touch screen is mounted, as compared to the existing method requiring an expensive exclusive analysis apparatus based on absorbance or fluorescence having a large volume, a skilled experimental technique such as electrophoresis, or a long analysis time to thereby be performed only in an experimental room equipped with specialists and equipment.

17 Claims, 6 Drawing Sheets

(56) References Cited

FOREIGN PATENT DOCUMENTS

| | | | |
|---|---|---|---|
| KR | 10-2010-0044384 A | 4/2010 | |
| KR | 10-2011-0000844 A | 1/2011 | |

OTHER PUBLICATIONS

Kwon, J., et al., "Information and Communications Policy", Jul. 16, 2008, pp. 1-16, vol. 20.

* cited by examiner

|   | [A] (ng/μL) | [B] (ng/μL) | Length (L) | Angle (θ) |
|---|---|---|---|---|
| 1 | 55.000 | 55.000 | 186.893 | 18.7258 |
| 2 | 55.000 | 55.000 | 172.351 | 17.9093 |
| 3 | 10.000 | 55.000 | 151.327 | 29.2753 |
| 4 | 100.000 | 55.000 | 191.901 | 15.4122 |
| 5 | 55.000 | 10.000 | 169.331 | 9.5179 |
| 6 | 55.000 | 55.000 | 175.915 | 20.2892 |
| 7 | 55.000 | 100.000 | 184.743 | 25.3167 |
| 8 | 55.000 | 55.000 | 176.264 | 20.5941 |
| 9 | 86.820 | 86.820 | 192.658 | 20.0339 |
| 10 | 55.000 | 55.000 | 174.568 | 19.0577 |
| 11 | 86.820 | 23.180 | 192.629 | 7.4571 |
| 12 | 23.180 | 23.180 | 126.649 | 15.5725 |
| 13 | 23.180 | 86.820 | 161.555 | 31.3287 |

METHOD FOR DETECTING BIOMOLECULES USING A CAPACITIVE TOUCH SCREEN

CROSS-REFERENCE TO RELATED APPLICATIONS

This application is a U.S. national phase under the provisions of 35 U.S.C. §371 of International Patent Application No. PCT/KR12/00220 filed Jan. 10, 2012, which in turn claims priority of Korean Patent Application No. 10-2011-0015268 filed Feb. 21, 2011. The disclosures of such international patent application and Korean priority patent application are hereby incorporated herein by reference in their respective entireties, for all purposes.

TECHNICAL FIELD

The present invention relates to a method of detecting biomolecules using a capacitive touch screen receiving a touch with a conductor as an input signal to perform an output on a display screen, and more particularly, to a method of detecting target biomolecules by applying biomolecules having electrical conductivity to a touch panel and detecting a change in capacitance of a surface of a touch panel generated according to the concentration of the biomolecules.

BACKGROUND ART

A touch screen is a device that may detect a position when a user's hand or an object is touched to characters or specific positions displayed on a screen without using an input device such as a keyboard or a mouse and perform a specific function.

The touch screen is basically configured of a touch panel, a touch controller, a driver soft ware (SW), and the like. The touch panel serves to determine the presence or absence of touch input, to detect input coordinates, and to transfer a signal to the touch controller, the controller serves to convert the signal transferred from the touch panel to a digital signal and output coordinates on a display, and the driver SW is a program allowing the touch panel to receive the digital signal from the controller to thereby be implemented appropriately for each of the operation systems.

The touch screen is divided into a resistive type touch screen, a capacitive touch screen, a surface acoustic wave (SAW) type touch screen, an infrared (IR) type touch screen, or the like, according to the implementation type of the touch panel.

The resistive type touch screen has a structure in which two substrates including a transparent electrode coated thereon are attached to each other, and operates in a manner of recognizing a position through an electric signal generated when pressure is applied to the resistive type touch screen by a finger or a pen and thus upper and lower electrode layers are touched to each other. This resistive type touch screen is cheap, accurate, and advantageous in miniaturization. The capacitive touch screen operates in a manner of detecting static electricity generated from human body and has strong durability, a short reaction time, and excellent transmittance. The SAW type touch screen operates in a manner of detecting a decrease in amplitude of an emitted surface acoustic wave when the surface acoustic wave reaches an obstacle and has excellent light transmittance, accuracy, and visibility. Further, in the IR type touch panel, a light emitting device and a light detecting device are disposed so as to face each other to recognize coordinates blocked by touch, and the IR type touch panel may be implemented only by a single sheet of glass without an indium tin oxide (ITO) film, or the like, such that transmittance may be at the highest level (Kwon Ji In et al., Information and Communications Policy, 20, 2008).

Particularly, the capacitive touch screen is an input device recently and widely used in various small-sized terminals such as a smart phone, a tablet PC, or the like (FIG. 1). More specifically, the principle of the capacitive touch screen is as follows. After applying a predetermined voltage from a touch controller to four corners of a touch panel to form a capacitive layer on a surface of the touch panel and touching this panel with a conductor (human body, mainly a finger), or the like, to change capacitance at a touch site, the touch controller detects this change and calculates a touch position to output the detected change amount and the calculated touch position on an external display device.

Meanwhile, currently, an in vitro diagnosis field for analyzing biomolecules associated with various diseases is a field for examining a health state and progression state of a disease in addition to early diagnosis of various diseases and is actively used in disease group selection and disease prevention, diagnosis and treatment monitoring, individual health state examination, and genetic examination, and veterinary medicine, environment management, food management, or the like, as a non-medical field. Recently, a highly infectious disease such as a disease caused by a mutant influenza virus, a foot-and-mouth disease, or the like, has been prevalent, which has generated a national crisis, and a demand for improving quality of life has increased, such that a demand for treatment monitoring or regular health checkup and importance thereof have been highlighted. Therefore, since a technology of analyzing the biomolecules associated with various diseases is economically and technologically significantly important and has a significant industrial ripple effect, the technology of analyzing the biomolecules has been actively studied globally.

Currently, in the in vitro diagnosis field, an assay method such as real-time polymerase chain reaction (real-time PCR) assay, enzyme-linked immonosorbent assay (ELISA), or the like, has been most prevalently used, but these assay methods require an analysis apparatus having a large volume or high cost or a skilled technique in the art or a long analysis time. Therefore, currently, most of the in vitro diagnosis may be performed only at a university/general hospital or a professional diagnostic center, which is equipped with professional equipments and professionals, and it takes a large amount of time and cost from sampling process to providing information of the result. In order to overcome this limitation, a point-of-care testing (POCT) system capable of being utilized in a local small hospital and a health center, or in home should be implemented. To this end, the development of a cheap and small sized analysis apparatus capable of simply performing in vitro molecular analysis has been demanded.

Therefore, the present inventors have tried to develop a method of detecting biomolecules capable of simply performing in vitro molecular analysis in a home instead of the existing in vitro diagnosis apparatus requiring a professional analysis apparatus and professional technique. As a result, the present inventors confirmed that in the case of touching biomolecules of which electric conductivity is changed according to the concentration to a capacitive touch screen to directly/indirectly measure capacitance of the touch panel changed according to the concentration, the corresponding biomolecules may be detected and quantified, thereby completing the present invention.

DISCLOSURE OF INVENTION

An object of the present invention is to provide a method of cheaply and simply detecting biomolecules using a touch screen.

The present invention provides a method of detecting biomolecules using a capacitive touch screen, comprising applying a sample on a touch panel of the capacitive touch screen and detecting a presence or a concentration of biomolecules in the sample.

According to an aspect of the present invention, there is provided a method of detecting biomolecules using a single-touch capacitive touch screen, the method including: (a) applying a standard sample and at least one biomolecule to be detected on a touch panel of the single-touch capacitive touch screen; (b) laminating an auxiliary panel on which a transparent electrode connected to a wire is coated or an auxiliary panel of which a transparent electrode is coated on both surfaces on the touch panel in step (a) so that the surface coated with the transparent electrode contacts with the touch panel; (c) touching the wire connected to the transparent electrode or the transparent electrode on the surface opposite to the surface in contact with the touch panel using a touch conductor to allow capacitance of a surface of the touch panel to be changed; and (d) measuring a touch signal position using a touch controller to detect a concentration of the biomolecule.

According to another aspect of the present invention, there is provided a method of detecting biomolecules using a single-touch capacitive touch screen, the method including: (a) applying biomolecules to be detected on a touch panel of the single-touch capacitive touch screen; (b) laminating an auxiliary panel on which a transparent electrode connected to a wire is coated or an auxiliary panel of which a transparent electrode is coated on both surfaces on the touch panel in step (a) so that the surface coated with the transparent electrode contacts with the touch panel; (c) touching the wire connected to the transparent electrode or the transparent electrode on the surface opposite to the surface in contact with the touch panel using a touch conductor to allow capacitance of a surface of the touch panel to be changed; and (d) measuring a touch signal position and a change amount in capacitance corresponding to the touch signal position using a touch controller further including an analog signal output device measuring and outputting the change amount in capacitance of the touch panel to thereby detect a concentration of the biomolecule.

According to another aspect of the present invention, there is provided a method of detecting biomolecules using a single-touch capacitive touch screen, the method including: (a) laminating an analysis frame including a sample inlet, a sample moving channel, a sample contact position, and a purification membrane but not having conductivity on a touch panel of the single-touch capacitive touch screen; (b) laminating an auxiliary panel on which a transparent electrode connected to a wire is coated or an auxiliary panel of which a transparent electrode is coated on both surfaces on the analysis frame in step (a) so that the surface coated with the transparent electrode contacts with the analysis frame; (c) injecting biomolecules to be detected into the sample inlet; (d) touching the wire connected to the transparent electrode or the transparent electrode on the surface opposite to the surface in contact with the touch panel using a touch conductor to allow capacitance of a surface of the touch panel to be changed; and (e) measuring a touch signal position and a change amount in capacitance corresponding to the touch signal position using a touch controller further including an analog signal output device measuring and outputting the change amount in capacitance of the touch panel to thereby detect a concentration of the biomolecule.

According to another aspect of the present invention, there is provided a method of detecting biomolecules using a multi-touch capacitive touch screen, the method including: (a) applying at least one biomolecule to be detected on a touch panel of the multi-touch capacitive touch screen; (b) laminating an auxiliary panel on which a transparent electrode connected to a wire is coated or an auxiliary panel of which a transparent electrode is coated on both surfaces on the touch panel in step (a) so that the surface coated with the transparent electrode contacts with the touch panel; (c) touching the wire connected to the transparent electrode or the transparent electrode on the surface opposite to the surface in contact with the touch panel using a touch conductor to allow capacitance of a surface of the touch panel to be changed; and (d) measuring at least one touch signal position and change amounts in capacitance corresponding to the touch signal positions using a touch controller further including an analog signal output device measuring and outputting the change amount in capacitance of the touch panel to detect a concentration of the biomolecule.

According to another aspect of the present invention, there is provided a method of detecting biomolecules using a multi-touch capacitive touch screen, the method including: (a) fixing probes binding to at least one target biomolecule, respectively, onto a touch panel of the multi-touch capacitive touch screen; (b) laminating an analysis frame including a sample inlet and a reaction chamber but not having conductivity on the touch panel to which the probes are fixed, and then laminating an auxiliary panel on which a transparent electrode connected to a wire is coated or an auxiliary panel of which a transparent electrode is coated on both surfaces on the analysis frame in step (a) so that the surface coated with the transparent electrode contacts with the analysis frame; (c) injecting biomolecules to be detected into the sample inlet; (d) touching the wire connected to the transparent electrode or the transparent electrode on the surface opposite to the surface in contact with the touch panel using a touch conductor to allow capacitance of a surface of the touch panel to be changed; and (e) measuring capacitance changed by binding between the probes and the injected biomolecules using a touch controller further including an analog signal output device measuring and outputting a change amount in capacitance of the touch panel to thereby detect the biomolecule.

According to another aspect of the present invention, there is provided an apparatus for detecting biomolecules, the apparatus including a capacitive touch screen on which a sample containing biomolecules is dropped; and an auxiliary panel on which a transparent electrode connected to a wire in contact with a touch conductor is coated or an auxiliary panel of which a transparent electrode is coated on both surfaces.

BEST MODE FOR CARRYING OUT THE INVENTION

Figure 1:
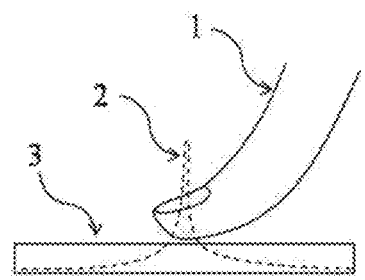
FIG. 1 shows the principle of allowing a signal to be inputted by a change in capacitance of a touch panel caused by directly touching the touch panel with a finger in a general touch screen system according to the related art.

In one aspect, the present invention relates to a method of detecting biomolecules using a single-touch capacitive touch screen, the method including: (a) applying a standard sample and at least one biomolecule to be detected on a touch panel of the single-touch capacitive touch screen; (b) laminating an auxiliary panel on which a transparent electrode connected to a wire is coated or an auxiliary panel of which a transparent electrode is coated on both surfaces on the touch panel in step (a) so that the surface coated with the transparent electrode contacts with the touch panel; (c) touching the wire connected to the transparent electrode or the transparent electrode on the surface opposite to the surface in contact with the touch panel using a touch conductor to allow capacitance of a surface of the touch panel to be changed; and (d) measuring a touch signal position using a touch controller to detect a concentration of the biomolecule.

According to the present invention, the standard sample may be an electrolyte solution of which a concentration is known, and the biomolecule may be selected from a group consisting of nucleic acid, protein, an inorganic ion in a body, and a mixture thereof.

According to the present invention, a material of the auxiliary panel may be selected from a group consisting of glass, acrylic, and plastic, and a material of the transparent electrode may be selected from a group consisting of indium-tin-oxide (ITO), zinc-oxide (ZnO), indium-zinc-oxide (IZO), gallium-zinc-oxide (GZO), aluminum-zinc-oxide (AZO), carbon nanotube (CNT), and graphene.

According to the present invention, the touch conductor may be selected from a group consisting of a finger, and a stylus pen and touch gloves that may be applied to the capacitive touch screen. Further, in step (d), the concentration of the biomolecule may be calculated by measuring the distance L and angle θ between the touch signal position on the touch panel measured using the touch controller and the position of the standard sample applied onto the touch panel and then inserting the measured distance L and angle θ into an equation obtained using the standard sample containing the biomolecule to be detected.

In the capacitive touch screen, even in the case of touching the touch screen via a material having electric conductivity, capacitance of the surface of the touch panel is changed, which is recognized as an input signal, and this change in capacitance is in proportion to electric conductivity of the corresponding material. Therefore, since the capacitive touch screen recognizes a touch with the conductor, the capacitive touch screen may also recognize a touch via an electrolyte solution.

Meanwhile, electric conductivity of the electrolyte solution is changed according to a concentration of ions dissolved in the solution. Since the biomolecule acts as an electrolyte in a state in which the biomolecule is dissolved in a solution, electric conductivity may also be changed according to the concentration of the biomolecule.

Figure 2:
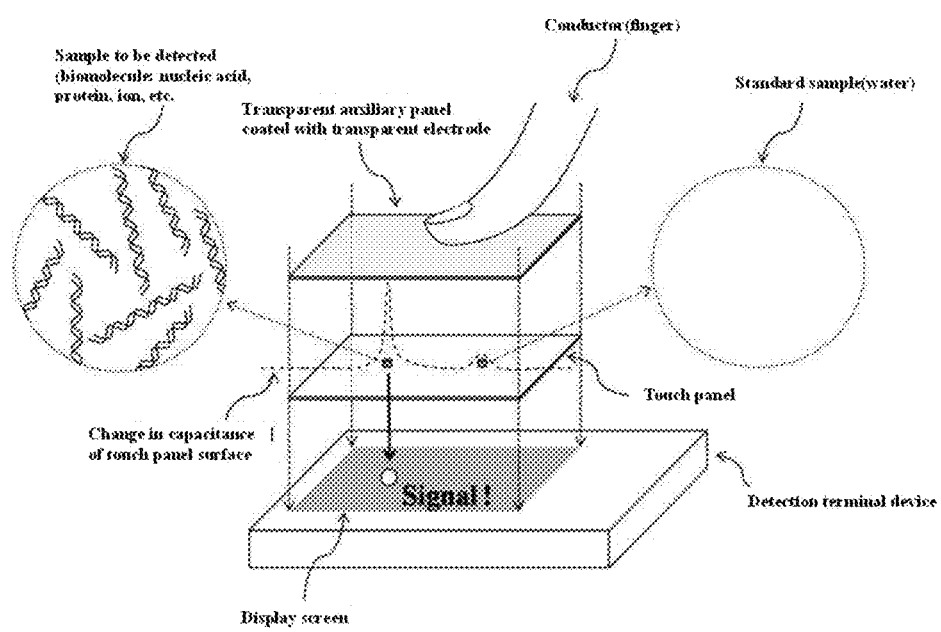
FIG. 2 is a mimetic diagram showing a method of detecting biomolecules using a capacitive touch screen.

Therefore, even in the case of dropping the biomolecule on the touch panel and touching an end of the drop with a finger instead of directly touching the surface of the touch panel, the touch signal may be generated (FIG. 2).

In the case of the single-touch capacitive touch screen, when two points are simultaneously touched with fingers, each of the points is not individually recognized, but a central point of the two points is recognized as the touch position. The reason is that two fingers have the same electric conductivity as each other. In the case of touching two points via electrolytes having different concentrations from each other by the same scheme, the touch position is recognized from the central position of the two points toward a point at which electric conductivity is higher, and the recognized position is also changed according to a difference in the concentration.

Figure 3:
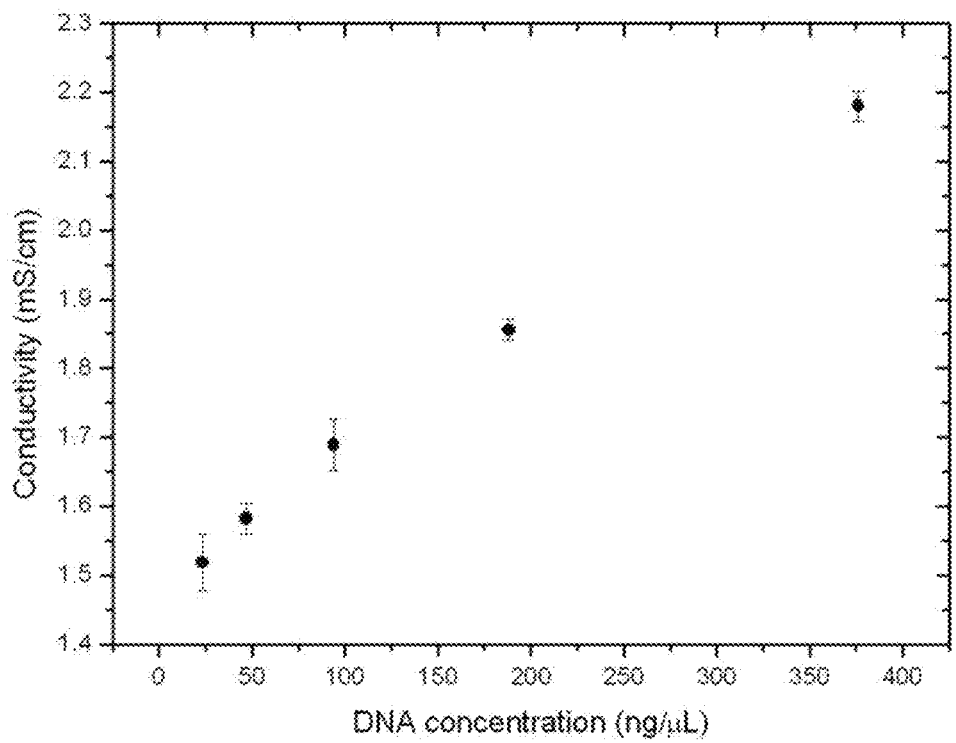
FIG. 3 is a graph showing a change in electric conductivity according to the change in concentration of a nucleic acid solution.

In the Example of the present invention, a change in electric conductivity according to the concentration of a biomolecule was measured, and as a result, it was confirmed that as the concentration of the biomolecule increased, electric conductivity also increased (FIG. 3).

Therefore, in the case of using a solution of which a concentration is already known as a standard sample and dropping an unknown biomolecule onto a predetermined point to be touched simultaneously with the standard sample, a touch signal is generated between the two points. Therefore, the concentration of the biomolecule may be measured by measuring a touch signal position between the two points using the touch controller. In addition, in the case in which the number of unknown samples is two, the two unknown samples may be simultaneously measured by measuring a touch signal position generated when the standard sample and the two unknown samples are dropped onto the predetermined points and these points are simultaneously touched.

Figure 4:
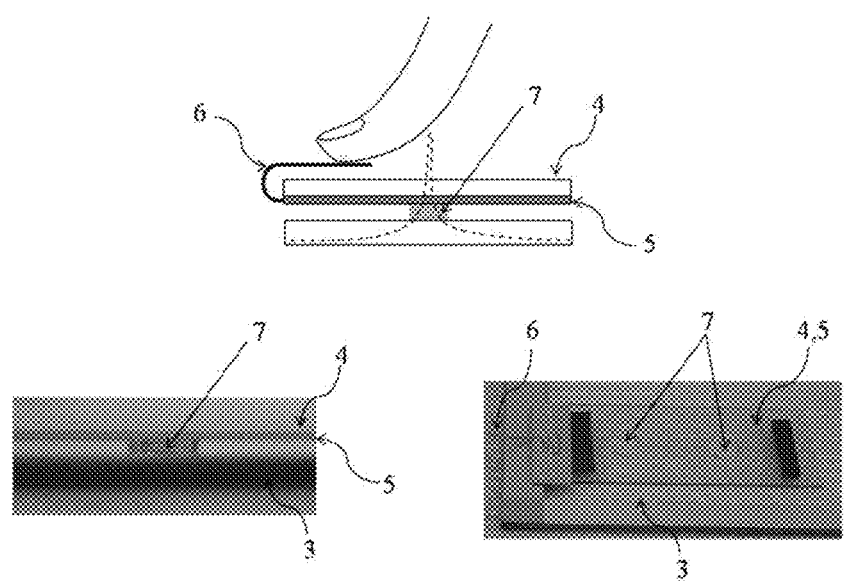
FIG. 4 shows the principle of allowing a signal to be inputted by a change in capacitance of a touch panel due to a touch with biomolecules and an actual photograph of the touch panel.

The principle of allowing a signal to be inputted by a change in capacitance of a touch panel caused by a touch with biomolecules and an actual photograph of the touch panel are shown in FIG. 4.

Figure 5:
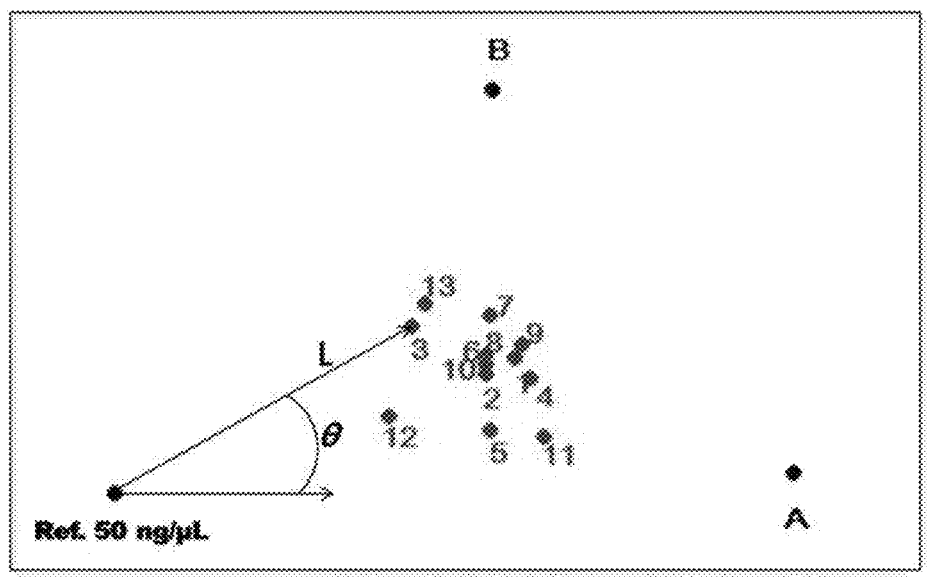
FIG. 5 shows positions recognized according to the various concentrations of two kinds of nucleic acid samples A and B and distances L and angles θ between positions of standard samples (50 ng/μl) and the recognized positions, respectively, using a single-touch capacitive touch screen system.
Figure 6:
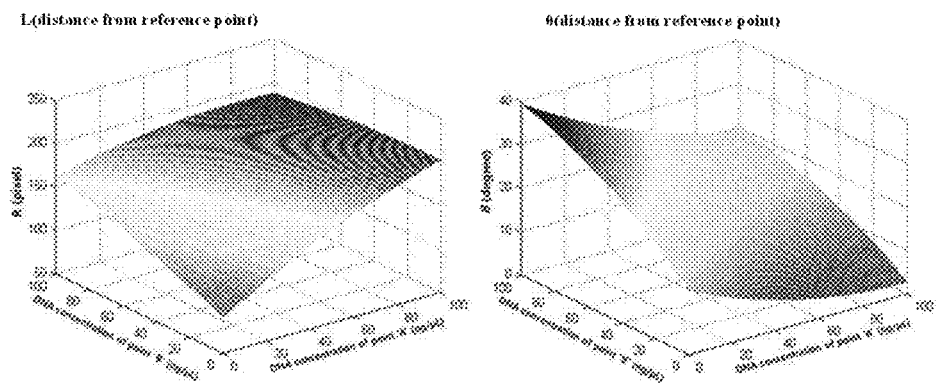
FIG. 6 shows equations of L values and θ values according to the concentration of two kinds of nucleic acid samples A and B and graphs showing a relationship between the concentrations of two nucleic acid samples and the L values and a relationship between the concentrations of two nucleic acid samples and the θ values, respectively.

In the Example of the present invention, in order to confirm that concentrations of two unknown samples may be simultaneously measured using the single-touch capacitive touch screen, 1 µl of nucleic acid solutions A and B having various concentrations in a range of 10 to 100 ng/µl were dropped onto predetermined positions of a touch panel of a single-touch capacitive touch screen, respectively, and a standard nucleic acid solution (50 ng/µl) was dropped onto another predetermined position. Then, an auxiliary panel coated with a transparent electrode was covered on the touch panel so that the transparent electrode contacts with the samples, and three points were simultaneously touched by touching a wire connected to the transparent electrode using a finger, thereby confirming a touch position between the three points (FIG. 5). In addition, distances L and angles θ between positions recognized as touch signal positions according to the concentrations of two kinds of nucleic acid solutions and the standard sample position were measured, respectively, and then as shown in the following Equations, an equation of L values and an equation of values according to the concentration were obtained using the measured L and θ values, respectively. Further, a graph showing a relationship between the concentrations of the two nucleic acid solutions and the L value and a graph showing a relationship between the concentrations of the two nucleic acid solutions and the θ value were obtained, respectively (FIG. 6).

In the Example of the present invention, as the capacitive touch screen, a single-touch capacitive touch screen (ES-CAP7000, eGALAX) including a touch panel and a touch controller was used, but the present invention is not limited thereto. Any touch screen may be used as long as the touch screen is a capacitive touch screen.

$$L = 88.0426 + 1.5454[A] + 0.8669[B] - 0.0042[A]^2 - 0.0015[B]^2 - 0.0086[A][B] \quad \text{Equation 1}$$

$$\theta = 14.1944 - 0.2398[A] + 0.32802[B] + 0.0012[A]^2 - 0.0013[B]^2 - 0.0008[A][B] \quad \text{Equation 2}$$

In Equations, [A] is a concentration of the nucleic acid solution A, and [B] is a concentration of the nucleic acid solution B.

Therefore, concentrations of two unknown biomolecules may be simultaneously measured by measuring a touch signal position generated by dropping the standard sample and two unknown samples and simultaneously touching them, measuring a distance L and an angle θ between the position of the standard sample (50 ng/µl) applied onto the touch panel and the measured touch signal position, and then inserting the measured values into Equations 1 and 2.

Figure 7:
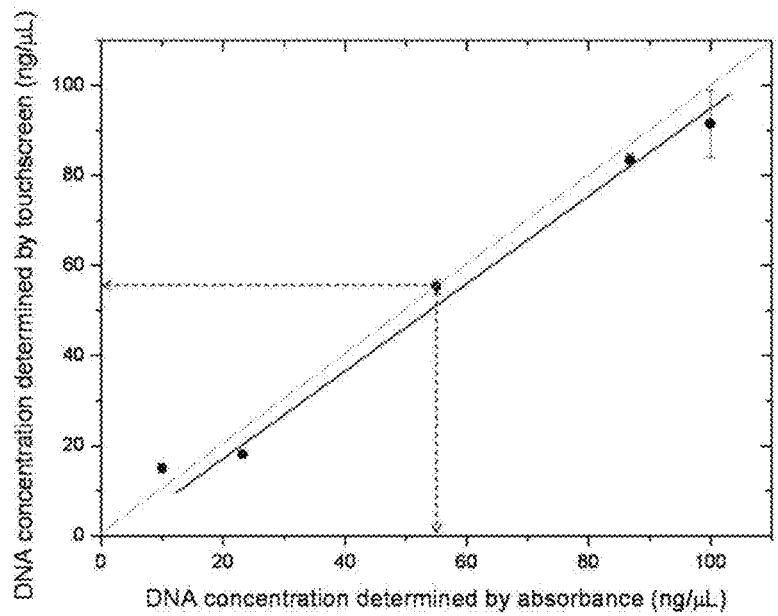
FIG. 7 is a graph of which the x axis is a value obtained by measuring a concentration of a *Chlamydia trachomatis* nucleic acid solution amplified by PCR using the existing method of analyzing nucleic acid based on absorbance and the y axis is a value obtained by measuring the concentration using the single-touch capacitive touch screen system using the relationship between the L values and θ values.

In the Examples of the present invention, a value obtained by measuring a concentration of *Chlamydia trachomatis* nucleic acid amplified by PCR using this method and a value obtained using the existing method of analyzing nucleic acid based on absorbance were compared with each other, and as a result, it was confirmed that the value obtained using the touch screen was similar to the value using method of analyzing nucleic acid based on absorbance (FIG. 7).

In another aspect, the present invention relates to a method of detecting biomolecules using a single-touch capacitive touch screen, the method including: (a) applying biomolecules to be detected on a touch panel of the single-touch capacitive touch screen; (b) laminating an auxiliary panel on which a transparent electrode connected to a wire is coated or an auxiliary panel of which a transparent electrode is coated on both surfaces on the touch panel in step (a) so that the surface coated with the transparent electrode contacts with the touch panel; (c) touching the wire connected to the transparent electrode or the transparent electrode on the surface opposite to the surface in contact with the touch panel using a touch conductor to allow capacitance of a surface of the touch panel to be changed; and (d) measuring a touch signal position and a change amount in capacitance corresponding to the touch signal position using a touch controller further including an analog signal output device measuring and outputting the change amount in capacitance of the touch panel to thereby detect a concentration of the biomolecule.

In the present invention, the biomolecule may be selected from a group consisting of nucleic acid, protein, an inorganic ion in a body, and a mixture thereof.

In the present invention, a material of the auxiliary panel may be selected from a group consisting of glass, acrylic, and plastic, and a material of the transparent electrode may be selected from a group consisting of indium-tin-oxide (ITO), zinc-oxide (ZnO), indium-zinc-oxide (IZO), gallium-zinc-oxide (GZO), aluminum-zinc-oxide (AZO), carbon nanotube (CNT), and graphene.

In the present invention, the touch conductor may be selected from a group consisting of a finger, and a stylus pen and touch gloves that may be applied to the capacitive touch screen, and the change amount in capacitance may be in proportion to the concentration of the biomolecule.

Figure 8:
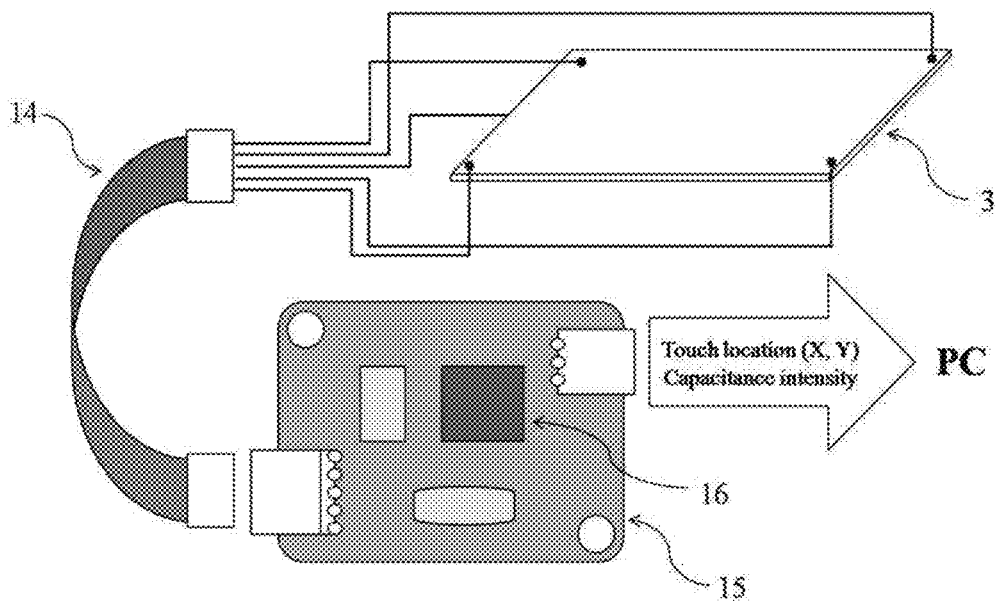
FIG. 8 is a mimetic diagram showing a touch controller including an analog signal output device directly outputting a change amount in capacitance of the touch panel added thereto to thereby be capable of outputting a touch position and a change amount in capacitance.

In a capacitive touch screen according to the related art, in order to recognize a change in capacitance as a touch signal, based on the predetermined change amount in capacitance, a change of the predetermined amount or more is determined in a controller as an effective input signal, and a change of the predetermined amount or less than is determined as noise, such that only a digital signal indicating touch ON/OFF is outputted. However, since the change amount in capacitance in the surface of the touch panel is different according to the concentration of biomolecules used for touch, in the case in which the analog signal output device capable of outputting the change amount in capacitance is added to the controller to directly output the change amount in capacitance of the touch panel, the concentration of the biomolecule may be measured. A mimetic diagram of the touch controller to which the analog signal output device capable of outing the change amount in capacitance is added is shown in FIG. 8.

In another aspect, the present invention relates to a method of detecting biomolecules using a single-touch capacitive touch screen, the method including: (a) laminating an analysis frame including a sample inlet, a sample moving channel, a sample contact position, and a purification membrane but not having conductivity on a touch panel of the single-touch capacitive touch screen; (b) laminating an auxiliary panel on which a transparent electrode connected to a wire is coated or an auxiliary panel of which a transparent electrode is coated on both surfaces on the analysis frame in step (a) so that the surface coated with the transparent electrode contacts with the analysis frame; (c) injecting biomolecules to be detected into the sample inlet; (d) touching the wire connected to the transparent electrode or the transparent electrode on the surface opposite to the surface in contact with the touch panel using a touch conductor to allow capacitance of a surface of the touch panel to be changed; and (e) measuring a touch signal position and a change amount in capacitance corresponding to the touch signal position using a touch controller further including an analog signal output device measuring and outputting the change amount in capacitance of the touch panel to thereby detect a concentration of the biomolecule.

Figure 9:
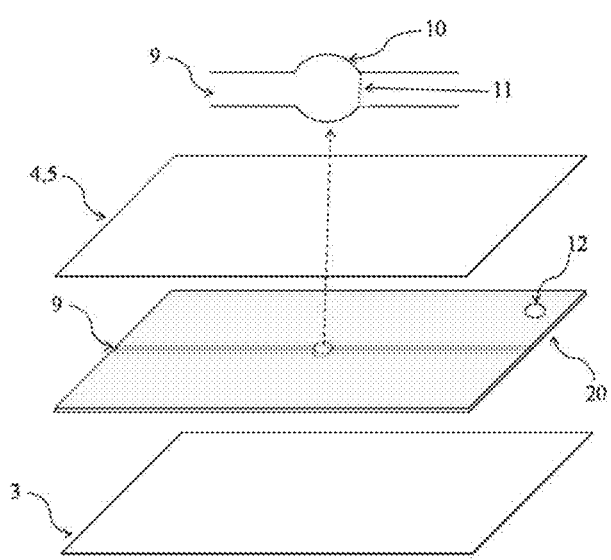
FIG. 9 shows a single-touch capacitive touch screen system in which a purification membrane capable of separating a specific biomolecule is included.

In the case of detecting a biomolecule containing other residues such as a mineral, or the like, since the detection result is significantly affected by other residues, necessarily, the biomolecule to be detected needs to be purified. Therefore, the analysis frame including the sample inlet, the sample moving channel, the sample contact position, and the purification membrane capable of separating the biomolecule and other residue from each other, but not having conductivity is used, such that the biomolecule may be detected only by injecting the sample without performing a complicated purification process (FIG. 9).

In the present invention, the biomolecule may be selected from a group consisting of nucleic acid, protein, an inorganic ion in a body, and a mixture thereof.

In the present invention, a material of the auxiliary panel may be selected from a group consisting of glass, acrylic, and plastic, and a material of the transparent electrode may be selected from a group consisting of indium-tin-oxide (ITO), zinc-oxide (ZnO), indium-zinc-oxide (IZO), gallium-zinc-oxide (GZO), aluminum-zinc-oxide (AZO), carbon nanotube (CNT), and graphene.

In the present invention, the touch conductor may be selected from a group consisting of a finger, and a stylus pen and touch gloves that may be applied to the capacitive touch screen, and the change amount in capacitance may be in proportion to the concentration of the biomolecule.

In another aspect, the present invention relates to a method of detecting biomolecules using a multi-touch capacitive touch screen, the method including: (a) applying at least one biomolecule to be detected on a touch panel of the multi-touch capacitive touch screen; (b) laminating an auxiliary panel on which a transparent electrode connected to a wire is coated or an auxiliary panel of which a transparent electrode is coated on both surfaces on the touch panel in step (a) so that the surface coated with the transparent electrode contacts with the touch panel; (c) touching the wire connected to the transparent electrode or the transparent electrode on the surface opposite to the surface in contact with the touch panel using a touch conductor to allow capacitance of a surface of the touch panel to be changed; and (d) measuring at least one touch signal position and change amounts in capacitance corresponding to the touch signal positions using a touch controller further including an analog signal output device measuring and outputting the change amount in capacitance of the touch panel to thereby detect a concentration of the biomolecule.

When several points of a touch panel are touched, since a multi-touch touch screen may recognize each of the points as touch signals unlike a single-touch touch screen, recently, the multi-touch touch screen is most frequently used in a smart phone, a tablet PC, and the like. In addition, since the multi-touch touch screen recognizes a change of the predetermined amount or more in capacitance to output only a digital signal similar to the single-touch capacitive touch screen, in the case in which the analog signal output device capable of directly outputting the change amount in capacitance is added to the controller, concentrations of several biomolecules may be measured. A system for simultaneously measuring concentrations of several biomolecules using a terminal based on a multi-touch capacitive touch screen mounted with a touch controller to which an analog signal output device are added is shown in FIG. 10.

Figure 10:
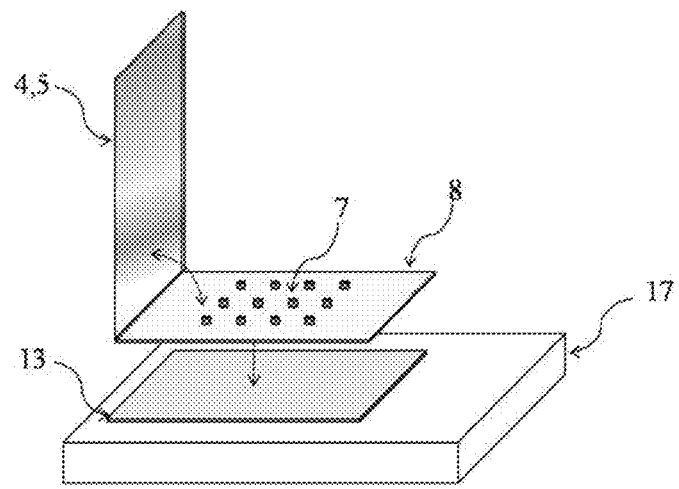
FIG. 10 shows a system capable of simultaneously measuring concentrations of several biomolecules using a terminal mounted with a multi-touch capacitive touch screen and a touch controller to which an analog signal output device is added.

As shown in FIG. 10, in the case of detecting the biomolecule using the terminal based on the capacitive touch screen, the biomolecule may be conveniently detected without contamination of the terminal by adhering a conductive adhesion film onto the terminal and then applying the sample instead of directly dropping a sample onto the terminal.

In the present invention, the biomolecule may be selected from a group consisting of nucleic acid, protein, an inorganic ion in a body, and a mixture thereof.

In the present invention, a material of the auxiliary panel may be selected from a group consisting of glass, acrylic, and plastic, and a material of the transparent electrode may be selected from a group consisting of indium-tin-oxide (ITO), zinc-oxide (ZnO), indium-zinc-oxide (IZO), gallium-zinc-oxide (GZO), aluminum-zinc-oxide (AZO), carbon nanotube (CNT), and graphene.

In the present invention, the touch conductor may be selected from a group consisting of a finger, and a stylus pen and touch gloves that may be applied to the capacitive touch screen, and the change amount in capacitance may be in proportion to the concentration of the biomolecule.

In another aspect, the present invention relates to a method of detecting biomolecules using a multi-touch capacitive touch screen, the method including: (a) fixing probes binding to at least one target biomolecule, respectively, onto a touch panel of the multi-touch capacitive touch screen; (b) laminating an analysis frame including a sample inlet and a reaction chamber but not having conductivity on the touch panel to which the probes are fixed, and then laminating an auxiliary panel on which a transparent electrode connected to a wire is coated or an auxiliary panel of which a transparent electrode is coated on both surfaces on the analysis frame in step (a) so that the surface coated with the transparent electrode contacts with the analysis frame; (c) injecting biomolecules to be detected into the sample inlet; (d) touching the wire connected to the transparent electrode or the transparent electrode on the surface opposite to the surface in contact with the touch panel using a touch conductor to allow capacitance of a surface of the touch panel to be changed; and (e) measuring capacitance changed by binding between the probes and the injected biomolecules using a touch controller further including an analog signal output device measuring and outputting a change amount in capacitance of the touch panel to thereby detect the biomolecule.

Figure 11:
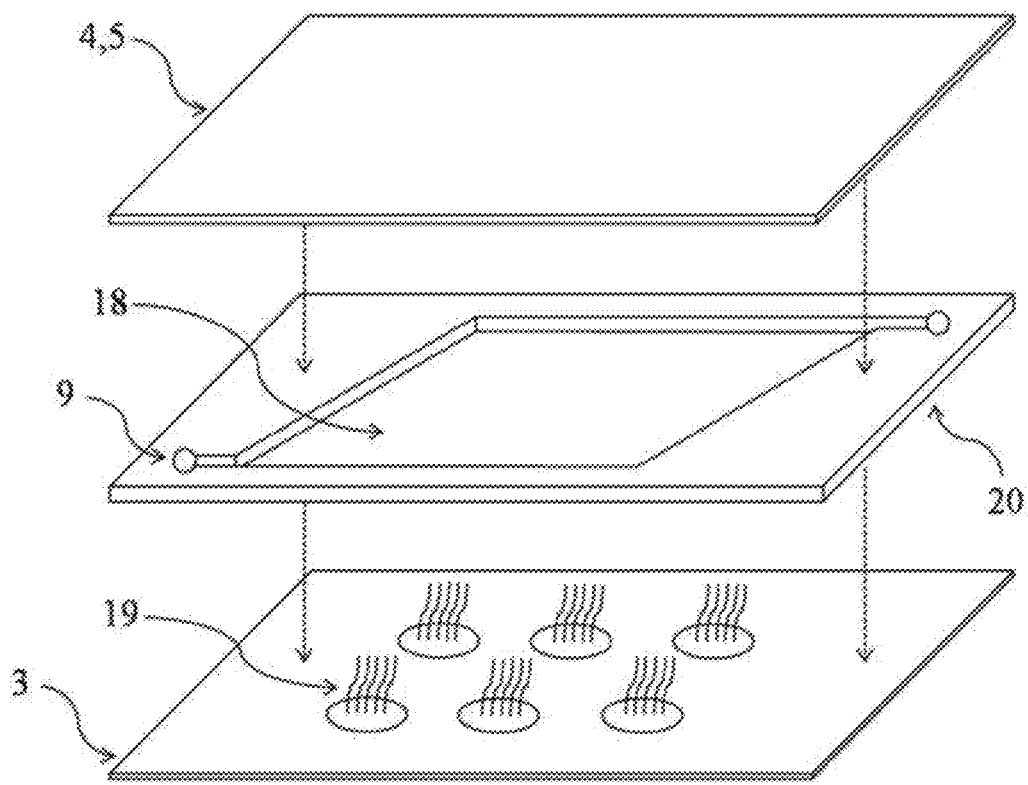
FIG. 11 shows a multi-touch capacitive touch screen system in which different kinds of probe materials specifically reacting with a biomolecule are fixed to a panel in order to detect unknown biomolecules.

In the case in which the nucleic acid is hybridized to thereby be present as double-stranded nucleic acid, electric conductivity of the nucleic acid is increased as compared to the case in which the nucleic acid is present as a single stranded nucleic acid. Therefore, in the case in which fixing the probes specifically binding to the target biomolecules to the touch panel of the multi-touch capacitive touch screen so as to have a predetermined pattern and reacting the probes fixed to the touch panel with the biomolecules to be detected to thereby be hybridized, electric conductivity at points at which the probes binding to the target biomolecule are positioned is increased, and capacitance at the points are changed, thereby being recognized as touch signals. The target biomolecule may be detected by confirming the probe at the position recognized as the touch signal position as described above (FIG. 11).

In the present invention, the biomolecule may be selected from a group consisting of nucleic acid, protein, and a mixture thereof.

In the present invention, a material of the auxiliary panel may be selected from a group consisting of glass, acrylic, and plastic, and a material of the transparent electrode may be selected from a group consisting of indium-tin-oxide (ITO), zinc-oxide (ZnO), indium-zinc-oxide (IZO), gallium-zinc-oxide (GZO), aluminum-zinc-oxide (AZO), carbon nanotube (CNT), and graphene.

In the present invention, the touch conductor may be selected from a group consisting of a finger, and a stylus pen and touch gloves that may be applied to the capacitive touch screen.

In another aspect, the present invention relates to an apparatus for detecting biomolecules, the apparatus including a capacitive touch screen on which a sample containing biomolecules is dropped; and an auxiliary panel on which a transparent electrode connected to a wire in contact with a touch conductor is coated or an auxiliary panel of which both surfaces are coated with a transparent electrode.

In the present invention, the capacitive touch screen may include a touch panel and a touch controller, wherein the touch controller further includes an analog signal output device measuring and outputting a change amount in capacitance of the touch panel.

In the present invention, the capacitive touch screen may be selected from a group consisting of a single-touch capacitive touch screen and a multi-touch capacitive touch screen, a material of the auxiliary panel may be selected from a group consisting of glass, acrylic, and plastic, and a material of the transparent electrode may be selected from a group consisting of indium-tin-oxide (ITO), zinc-oxide (ZnO), indium-zinc-oxide (IZO), gallium-zinc-oxide (GZO), aluminum-zinc-oxide (AZO), carbon nanotube (CNT), and graphene.

In the present invention, the biomolecule may be selected from a group consisting of nucleic acid, protein, an inorganic ion in a body, and a mixture thereof.

In the present invention, the apparatus for detecting biomolecules may further include an analysis frame not having conductivity, wherein the analysis frame includes a sample inlet, a sample moving channel, a sample contact position, and a purification membrane or includes a sample inlet and a reaction chamber.

EXAMPLES

Hereinafter, the present invention will be described in detail through the Examples. However, these Examples are only to illustrate the present invention, and those skilled in the art will appreciate that these Examples are not to be construed as limiting a scope of the present invention.

Example 1

Change in Electric Conductivity According to Concentration of Biomolecule

Since a capacitive touch screen recognizes a touch with a conductor, the capacitive touch screen may also recognize a touch via an electrolyte solution. That is, even in the case of dropping a drop of an electrolyte solution onto a touch panel and touch the drop with a finger instead of directly touch a surface of the touch panel, a touch signal is generated. The reason is that capacitance of the surface of the touch panel is changed according to electric conductivity of the electrolyte solution, and electric conductivity of the electrolyte solution is different according to the concentration of ions dissolved in the solution. Since the biomolecule acts as an electrolyte in a state in which the biomolecule is dissolved in a solution, electric conductivity is changed according to the concentration of the biomolecule.

In order to confirm that electric conductivity was changed according to the concentration of the biomolecule, *Chlamydia trachomatis* nucleic acid amplified by PCR was prepared so as to have various concentrations in a range of 25 to 375 ng/µl, and a resistance value of the nucleic acid solution according to the concentration was measured using a RMS multimeter (FLUKE 177), thereby calculating electric conductivity of each of the nucleic acid solution.

As a result, it was confirmed that as the concentration of the nucleic acid increased, electric conductivity also increased as shown in FIG. 3.

Therefore, in the case of directly/indirectly measuring a change in capacitance generated through a touch by a biomolecule solution, a concentration of the biomolecule in the solution may be measured.

Example 2

Detection of Biomolecule Using Single-Touch Capacitive Touch Screen

When two points of the single-touch capacitive touch screen are simultaneously touched with fingers, each of the points is not individually recognized, but a central point of the two points is recognized as the touch position. The reason is that two fingers have the same electric conductivity as each other. In the case of touching two points via electrolytes having different concentrations from each other by the same scheme, a touch position is recognized from the central position of the two points toward a point at which electric conductivity is higher, and the recognized position is changed according to a difference in the concentration. Therefore, in the case using a solution of which a concentration is already known as a standard solution, dropping an unknown biomolecule solution onto a predetermined point, and touching the biomolecule solution simultaneously with the standard solution, a touch signal is generated between the two points, and a concentration of the biomolecule in the unknown sample may be measured from the touch position and the concentration of the standard sample.

Further, in the case in which the number of unknown samples is two, the two unknown samples may be simultaneously measured by dropping the standard solution and the two unknown sample onto the predetermined positions, measuring a distance and an angle between a position of a touch signal generated at the time of simultaneously touching the standard solution and the two unknown samples and a position of the standard solution, and estimating concentrations of biomolecules in the two unknown samples.

In order to confirm that concentrations of two unknown samples may be simultaneously measured using the capacitive touch screen, a single-touch capacitive touch screen (ES-CAP7000, eGALAX) including a touch panel and a touch controller and slide glass (ASIA INC.) coated with indium-tin-oxide (ITO) as an auxiliary panel were prepared.

As the two unknown samples, nucleic acid solutions A and B having various concentrations in a range of 10 to 100 ng/µl were prepared, respectively, by amplifying *Chlamydia trachomatis* gene using PCR and purifying the amplified gene using a purification kit.

1 µl of the two nucleic acid solutions A and B having various concentrations in a range of 10 to 100 ng/µl were dropped onto two fixed points on the touch panel of the prepared touch screen, respectively, and a standard nucleic acid solution of which a concentration was controlled to 50 ng/µl by measuring absorbance after PCR-amplification/purification was dropped on to another fixed position. Thereafter, an auxiliary panel on which a transparent electrode is coated is covered on the touch panel so that the transparent panel contacted with the samples, and a wire connected to the transparent electrode was touched with a finger, thereby simultaneously touching three points on the touch panel on which the samples were dropped. Then, a single touch signal position between the three points was confirmed using the touch controller connected to the touch panel. Thereafter, the distance L and the angle θ between the point recognized as the touch position and the position of the standard solution were measured according to each of the concentrations of two kinds of nucleic acid solutions.

As a result, the distance L and the angle θ from the position of the standard solution were calculated from x and y coordinates (pixel) of each of the points on a PC monitor according to the concentrations of the two kinds of nucleic acid solution, as shown in FIG. 5. In addition, equations of L values and θ values according to the concentration of two kinds of nucleic acid samples, a graph showing a relationship between the concentrations of two nucleic acid samples and the L values, and a graph showing a relationship between the concentrations of two nucleic acid samples and the θ values, were obtained using a minitab, which is a statistics program, and using a matlab, which is a computing program (FIG. 6).

Further, the concentration of the *Chlamydia trachomatis* nucleic acid solution amplified by PCR was measured by measuring absorbance thereof was measured at 260 nm using a nanodrop ND-1000 spectrophotometer and compared with the value measured using the touch screen.

As a result, it was confirmed that the result measured using the touch screen was similar to the result using the method of analyzing nucleic acid based on absorbance according to the related art as shown in FIG. 7.

Although the present invention has been described in detail based on particular features thereof, and it is obvious to those skilled in the art that these specific technologies are merely preferable embodiments and thus the scope of the present invention is not limited to the embodiments. Therefore, the substantial scope of the present invention is defined by the accompanying claims and equivalent thereof.

DETAILED DESCRIPTION OF MAIN ELEMENTS

1. Finger
2. Change in capacitance of surface of touch panel by touch
3. Touch panel
4. Transparent auxiliary panel
5. Transparent electrode coating layer
6. Wire connected to electrode
7. Detection sample (biomolecule)
8. Conductive touch screen adhesion film
9. Sample inlet
10. Sample contact position
11. Purification membrane
12. Standard sample contact position
13. Touch screen of terminal
14. Cable
15. Touch controller
16. Analog signal output device
17. Apparatus (terminal, or the like) for detecting nucleic acid based on touch screen
18. Reaction chamber
19. Probe specifically binding to target biomolecule
20. Analysis frame

INDUSTRIAL APPLICABILITY

A method of detecting biomolecule according to the present invention uses a capacitive touch screen capable of being cheaply manufactured on a large scale, such that the method may have advantages such as cheap cost and a short analysis time and simply detect biomolecules in a personal terminal such as a smart phone, a tablet PC, and the like, on which a capacitive touch screen is mounted, as compared to the existing method requiring an expensive exclusive analysis apparatus based on absorbance or fluorescence having a large volume, a skilled experimental technique such as electrophoresis, or a long analysis time to thereby be performed only in an experimental room equipped with specialists and equipments.

The invention claimed is:

1. A method of detecting biomolecules using a single-touch capacitive touch screen, comprising:
   (a) applying a standard sample and at least one biomolecule to be detected on a touch panel of the single-touch capacitive touch screen;
   (b) laminating an auxiliary panel on which a transparent electrode connected to a wire is coated or an auxiliary panel of which a transparent electrode is coated on both surfaces on the touch panel in the step (a) thereby being the surface coated with the transparent electrode in contact with the touch panel;
   (c) touching the wire connected to the transparent electrode or the transparent electrode on the surface opposite to the surface in contact with the touch panel using a touch conductor to allow capacitance of a surface of the touch panel to be changed; and
   (d) measuring a touch signal position using a touch controller to detect a concentration of the biomolecule,
   wherein in the step (d), a concentration of the biomolecule is calculated by measuring a distance L and an angle θ between the touch signal position on the touch panel measured using the touch controller and the position of the standard sample applied onto the touch panel and then inserting the measured distance L and the angle θ into an equation obtained by the standard sample containing the biomolecule to be detected.

2. The method of detecting biomolecules of claim 1, wherein the standard sample is an electrolyte solution of which a concentration is known.

3. The method of detecting biomolecules of claim 1, wherein the biomolecule is selected from a group consisting of nucleic acid, protein, an inorganic ion in a body, and a mixture thereof.

4. The method of detecting biomolecules of claim 1, wherein the auxiliary panel is made of one selected from a group consisting of glass, acrylic, and plastic.

5. The method of detecting biomolecules of claim 1, wherein the transparent electrode is made of one selected from a group consisting of indium-tin-oxide (ITO), zinc-oxide (ZnO), indium-zinc-oxide (IZO), gallium-zinc-oxide (GZO), aluminum-zinc-oxide (AZO), carbon nanotube (CNT) and graphene.

6. The method of detecting biomolecules of claim 1, wherein the touch conductor is selected from a group consisting of a finger, a stylus pen applicable to a capacitive touch screen and touch gloves applicable to a capacitive touch screen.

7. A method of detecting biomolecules using a multi-touch capacitive touch screen, comprising:
   (a) applying at least one biomolecule to be detected on a touch panel of the multi-touch capacitive touch screen;
   (b) laminating an auxiliary panel on which a transparent electrode connected to a wire is coated or an auxiliary panel of which a transparent electrode is coated on both surfaces on the touch panel in the step (a) thereby being the surface coated with the transparent electrode in contact with the touch panel;
   (c) touching the wire connected to the transparent electrode or the transparent electrode on the surface opposite to the surface in contact with the touch panel using a touch conductor to allow capacitance of a surface of the touch panel to be changed; and (d) measuring at least one touch signal position and change amounts in capacitance corresponding to the touch signal positions using a touch controller further comprising an analog signal output device which measures and outputs the change amount in capacitance of the touch panel, thereby detecting a concentration of the biomolecule, wherein in the step (d), a concentration of the biomolecule is calculated by measuring a distance L and an angle θ between the touch signal position on the touch panel measured using the touch controller and the position of the standard sample applied onto the touch panel and then inserting the measured distance L and the angle θ into an equation obtained by the standard sample containing the biomolecule to be detected.

8. The method of detecting biomolecules of claim 7, wherein the biomolecule is selected from a group consisting of nucleic acid, protein, an inorganic ion in a body, and a mixture thereof.

9. The method of detecting biomolecules of claim 7, wherein the auxiliary panel is made of one selected from a group consisting of glass, acrylic, and plastic.

10. The method of detecting biomolecules of claim 7, wherein the transparent electrode is made of one selected from a group consisting of indium-tin-oxide (ITO), zinc-oxide (ZnO), indium-zinc-oxide (IZO), gallium-zinc-oxide (GZO), aluminum-zinc-oxide (AZO), carbon nanotube (CNT) and graphene.

11. The method of detecting biomolecules of claim 7, wherein the touch conductor is selected from a group consisting of a finger, a stylus pen applicable to a capacitive touch screen and touch gloves applicable to a capacitive touch screen.

12. The method of detecting biomolecules of claim 7, wherein the change amount in capacitance is in proportion to the concentration of the biomolecule.

13. A method of detecting biomolecules using a multi-touch capacitive touch screen, comprising:
(a) fixing probes respectively bound to at least one target biomolecule, onto a touch panel of the multi-touch capacitive touch screen;
(b) laminating an nonconductive analysis frame including a sample inlet and a reaction chamber on the touch panel to which the probes are fixed, and then laminating an auxiliary panel on which a transparent electrode connected to a wire is coated or an auxiliary panel of which a transparent electrode is coated on both surfaces on the analysis frame in the step (a) thereby the surface coated with the transparent electrode in contact with the analysis frame;
(c) injecting biomolecules to be detected into the sample inlet;
(d) touching the wire connected to the transparent electrode or the transparent electrode on the surface opposite to the surface in contact with the touch panel using a touch conductor to allow capacitance of a surface of the touch panel to be changed; and
(e) measuring capacitance changes by binding the probes to the injected biomolecules using a touch controller further comprising an analog signal output device which measures and outputs a change amount in capacitance of the touch panel to, thereby detecting the biomolecule, wherein in the step (e), a concentration of the biomolecule is calculated by measuring a distance L and an angle θ between the touch signal position on the touch panel measured using the touch controller and the position of the standard sample applied onto the touch panel and then inserting the measured distance L and the angle θ into an equation obtained by the standard sample containing the biomolecule to be detected.

14. The method of detecting biomolecules of claim 13, wherein the biomolecule is selected from a group consisting of nucleic acid, protein, an inorganic ion in a body, and a mixture thereof.

15. The method of detecting biomolecules of claim 13, wherein the auxiliary panel is made of one selected from a group consisting of glass, acrylic, and plastic.

16. The method of detecting biomolecules of claim 13, wherein the transparent electrode is made of one selected from a group consisting of indium-tin-oxide (ITO), zinc-oxide (ZnO), indium-zinc-oxide (IZO), gallium-zinc-oxide (GZO), aluminum-zinc-oxide (AZO), carbon nanotube (CNT) and graphene.

17. The method of detecting biomolecules of claim 13, wherein the touch conductor is selected from a group consisting of a finger, a stylus pen applicable to a capacitive touch screen and touch gloves applicable to a capacitive touch screen.

* * * * *

UNITED STATES PATENT AND TRADEMARK OFFICE
CERTIFICATE OF CORRECTION

| | |
|---|---|
| PATENT NO. | : 9,274,658 B2 |
| APPLICATION NO. | : 14/000403 |
| DATED | : March 1, 2016 |
| INVENTOR(S) | : Hyun Gyu Park et al. |

Page 1 of 1

It is certified that error appears in the above-identified patent and that said Letters Patent is hereby corrected as shown below:

Specification

Column 12, line 44: "(ASIA INC.)" should be --(ASTA INC.)--.

Signed and Sealed this
Nineteenth Day of July, 2016

Michelle K. Lee
*Director of the United States Patent and Trademark Office*